(12) United States Patent
Ito et al.

(10) Patent No.: US 8,106,222 B2
(45) Date of Patent: Jan. 31, 2012

(54) FLUORINE-CONTAINING ETHER COMPOUND

(75) Inventors: Takayuki Ito, Minami-ashigara (JP); Toshimitsu Sakuma, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 810 days.

(21) Appl. No.: 12/100,362

(22) Filed: Apr. 9, 2008

(65) Prior Publication Data

US 2009/0018350 A1    Jan. 15, 2009

(51) Int. Cl.
   *C07D 321/00* (2006.01)
(52) U.S. Cl. .......................... 549/334; 549/300
(58) Field of Classification Search .................. 549/330, 549/334
   See application file for complete search history.

(56) References Cited

U.S. PATENT DOCUMENTS

| | | | |
|---|---|---|---|
| 4,076,916 A | 2/1978 | Lagow | |
| 4,523,039 A * | 6/1985 | Lagow et al. | 568/615 |
| 4,736,045 A * | 4/1988 | Drakesmith et al. | 549/380 |
| 5,506,309 A * | 4/1996 | Bierschenk et al. | 525/410 |

FOREIGN PATENT DOCUMENTS

| | | |
|---|---|---|
| JP | 2000-95862 | 4/2000 |
| JP | 2002-332309 | 11/2002 |
| WO | 90/03353 A1 | 4/1990 |

\* cited by examiner

*Primary Examiner* — Andrew D Kosar
*Assistant Examiner* — Raymond Covington
(74) *Attorney, Agent, or Firm* — Sughrue Mion, PLLC

(57) ABSTRACT

A fluorine-containing ether compound with a fluorine content increased, the fluorine content being enhanced by fluorinating a polymer including a repeating unit represented by the following Formula (I):

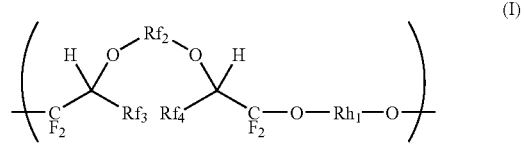

wherein $Rh_1$ represents a divalent linkage group; $Rf_2$ represents an perfluoroalkylene group; each of $Rf_3$ and $Rf_4$ independently represents a fluorine atom, a perfluoroalkyl group or a perfluoroalkoxy group, and any two of $Rf_2$, $Rf_3$ and $Rf_4$ may be combined with each other to form a ring.

5 Claims, No Drawings

FLUORINE-CONTAINING ETHER COMPOUND

FIELD OF THE INVENTION

The present invention relates to a highly fluorinated fluorine-containing ether compound.

BACKGROUND OF THE INVENTION

Fluorine-containing polymers can exhibit various properties that are not performed by polymers containing other atoms. Those properties include low refractive index, low dielectric constant, water- and oil-repellency, low hygroscopicity, chemical resistance, non-adhesiveness, low frictional properties, and electrical insulation properties. Those properties may vary depending on their structures and fluorine contents.

A most common method of synthesizing such fluorine-containing polymers is a method of conducting radical polymerization of fluorine-containing monomers. However, the kinds of generally available fluorine-containing monomers by synthesis are not sufficient, and those monomers, except for some of them, generally have low reactivity. Specifically, there is a significant limitation on the structure of the polymer that can be synthesized according to the radical polymerization of the fluorine-containing monomers.

As means to solve this problem, there are known methods of reacting a variety of polymers synthesized by a variety of methods with fluorine gas to obtain a fluorine-containing polymer. Typically, U.S. Pat. No. 4,076,916 and JP-A-2002-95862 ("JP-A" means unexamined published Japanese patent application) disclose methods of fluorination by direct contact of a solid polymer with fluorine gas. Those methods, however, fail to achieve homogeneous fluorination of the entire polymer, because fluorination of the surface of the polymer preferentially occurs. International Publication WO 90/03353 discloses an example in which a polymer is fluorinated in a liquid phase. The raw materials used are, however, hydrocarbon polyethers each having a molecular weight of about 2,000, and the document lacks an example that is applied to polymers having higher molecular weights. This is probably because such a high molecular weight polymer has low solubility in a fluorinated solvent, whereby the reaction does not proceed sufficiently. As a possible solution to this, JP-A-2002-332309 describes an example in which a fluorine component is introduced into a side chain of a polymer to improve the solubility of the polymer in a fluorinated solvent, whereby fluorination of a polymer having a relatively high molecular weight is achieved. However, the fluorine content of the produced polymer is not always satisfactorily high.

As described above, no synthesis method has been known, which easily and conveniently produces fluorine-containing compounds having various structures and high fluorine contents.

SUMMARY OF THE INVENTION

The present invention resides in a fluorine-containing ether compound with a fluorine content increased, the fluorine content being enhanced by fluorinating a polymer including a repeating unit represented by the following Formula (I):

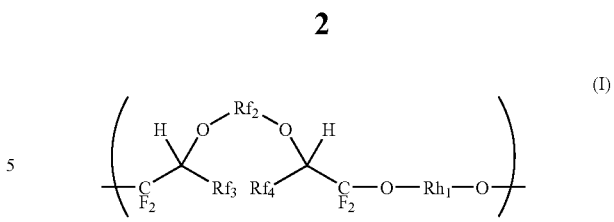

wherein $Rh_1$ represents a divalent linkage group; $Rf_2$ represents an perfluoroalkylene group; each of $Rf_3$ and $Rf_4$ independently represents a fluorine atom, a perfluoroalkyl group or a perfluoroalkoxy group, and any two of $Rf_2$, $Rf_3$ and $Rf_4$ may be combined with each other to form a ring.

Further, the present invention resides in a perfluoroether compound represented by the following Formula (IV):

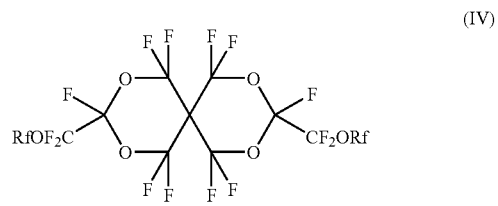

where Rf represents a perfluoroalkyl group.

Other and further features and advantages of the invention will appear more fully from the following description.

DETAILED DESCRIPTION OF THE INVENTION

The present invention provides the following means:

(1) A fluorine-containing ether compound with a fluorine content increased, the fluorine content being enhanced by fluorinating a polymer including a repeating unit represented by the following Formula (I):

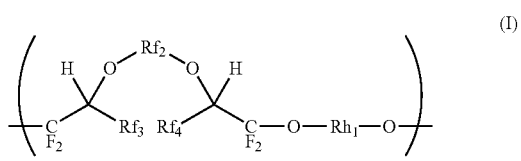

wherein $Rh_1$ represents a divalent linkage group; $Rf_2$ represents an perfluoroalkylene group; each of $Rf_3$ and $Rf_4$ independently represents a fluorine atom, a perfluoroalkyl group or a perfluoroalkoxy group, and any two of $Rf_2$, $Rf_3$ and $Rf_4$ may be combined with each other to form a ring.

(2) The fluorine-containing ether compound according to the item (1), in which the repeating unit represented by Formula (I) is a repeating unit represented by the following Formula (II):

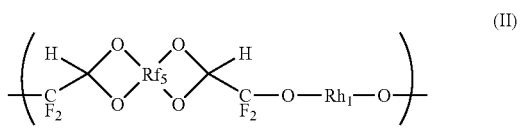

where $Rh_1$ is as defined above, and $Rf_5$ represents a tetravalent perfluorinated linkage group.

(3) The fluorine-containing ether compound according to the item (2), in which the repeating unit represented by Formula (II) is a repeating unit represented by the following Formula (III):

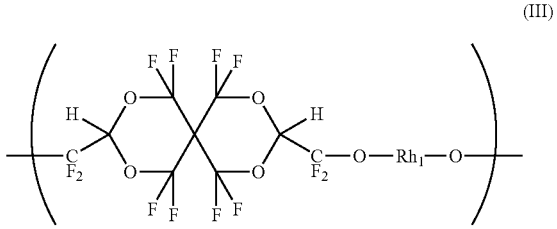

wherein $Rh_1$ is as defined above.

(4) The fluorine-containing ether compound according to any one of items (1) to (3), obtained by the reaction between a solution of a polymer having the repeating unit represented by Formula (I) and a fluorine gas.

(5) A perfluoroether compound represented by the following Formula (IV):

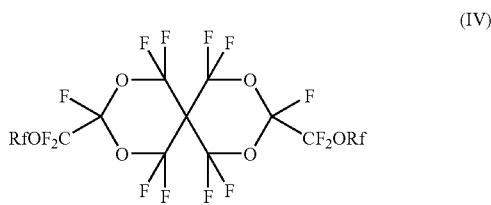

where Rf represents a perfluoroalkyl group.

Hereinafter, the present invention will be described in detail.

In Formula (I), $Rh_1$ represents a divalent linkage group and is preferably an alkylene group, an arylene group or a group containing any of these groups linked through another divalent linkage group (E).

Preferred alkylene group as $Rh_1$ is a substituted or unsubstituted alkylene group having 1 to 30 carbon atoms, which may be linear, branched or cyclic, and which may have an ether bond in the chain. The alkylene group has more preferably 1 to 20 carbon atoms, and still more preferably 2 to 10 carbon atoms.

Examples of the substituent of the alkylene group include halogen atoms (for example, a fluorine atom, a chlorine atom, a bromine atom and an iodine atom), alkyl groups having 20 or less carbon atoms (for example, methyl or ethyl), aryl groups having 30 or less carbon atoms (for example, phenyl or naphtyl), a cyano group, a carboxyl group, alkoxycarbony groups having 20 or less carbon atoms (for example, methoxycarbonyl), aryloxycarbony groups having 30 or less carbon atoms (for example, phenoxycarbony), carbamoyl groups (for example, a carbamoyl group, N-phenycarbamoyl group, N,N-dimethylcarbamoyl group), alkylcarbonyl groups having 20 or less carbon atoms (for example, acetyl), arylcarbonyl groups having 30 or less carbon atoms (for example, benzoyl), a nitro group, amino groups (for example, amino, dimethylamino, anilino), acylamino groups having 20 or less carbon atoms (for example, acetoamino and ethoxycarbonylamino), sulfonamido groups (for example, methanesulfonamido), imido groups (for example, succinimido and phthalimido), imino groups (for example, benzylideneimino), a hydroxy group, alkoxy groups having 20 or less carbon atoms (for example, methoxy), aryloxy groups having 30 or less carbon atoms (for example, phenoxy), acyloxy groups having 20 or less carbon atoms (for example, acetoxy), alkylsulfonyloxy groups having 20 or less carbon atoms (for example, methanesulfonyloxy), arylsulfonyloxy groups having 30 or less carbon atoms (for example, benzenesulfonyloxy), sulfo groups, sulfamoyl groups (for example, sulfamoyl and N-phenylsulfamoyl), alkylthio groups having 20 or less carbon atoms (for example, methylthio), arylthio groups having 30 or less carbon atoms (for example, phenylthio), alkylsulfonyl groups having 20 or less carbon atoms (for example, methanesulfonyl), arylsulfonyl groups having 30 or less carbon atoms (for example, benzenesulfonyl), and heterocyclic groups. The substituent may be further substituted. When plural substituents are present, they may be the same or different. Further, any two of these substituents may be combined with each other to form a ring.

As a substituent, a halogen atom is preferred, and a fluorine atom is more preferred.

Preferred arylene group as $Rh_1$ is a substituted or unsubstituted arylene group having 6 to 30 carbon atoms. An arylene group having 6 to 20 carbon atoms is more preferred, and an arylene group having 6 to 10 carbon atoms is still more preferred. Examples of the substituents are as above.

Examples of the other divalent linkage group connecting an alkylene group and/or an arylene group include an alkylene group, an arylene group, —O—, —S—, —CO—, —SO—, —SO$_2$— and a bond (single bond).

$Rh_1$ is preferably an alkylene group or arylene group which is substituted with at least one fluorine atom and is more preferably an alkylene group represented by —CH$_2$Rf$_{11}$CH$_2$—. Rf$_{11}$ is a perfluoroalkylene group having 1 to 28 carbon atoms, which may be linear, branched or cyclic, and which may have an ether bond in its chain. The perfluoroalkylene group has preferably 1 to 18 carbon atoms, and more preferably 2 to 8 carbon atoms.

Specific examples of $Rh_1$ will be illustrated below, but the present invention is not limited thereto. In the following formulae, the asterisk "*" represents the bonding position with an oxygen atom. When there is a possibility that a plurality of stereoisomers exist, $Rh_1$ may be one of such stereoisomers or a mixture of a plurality of stereoisomers.

(Rh$_1$-1)

(Rh$_1$-2)

(Rh$_1$-3)

(Rh$_1$-4)

(Rh$_1$-5)

(Rh$_1$-6)

(Rh$_1$-7)

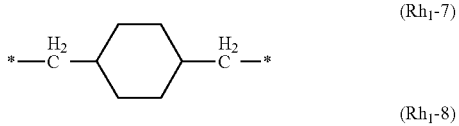

(Rh$_1$-8)

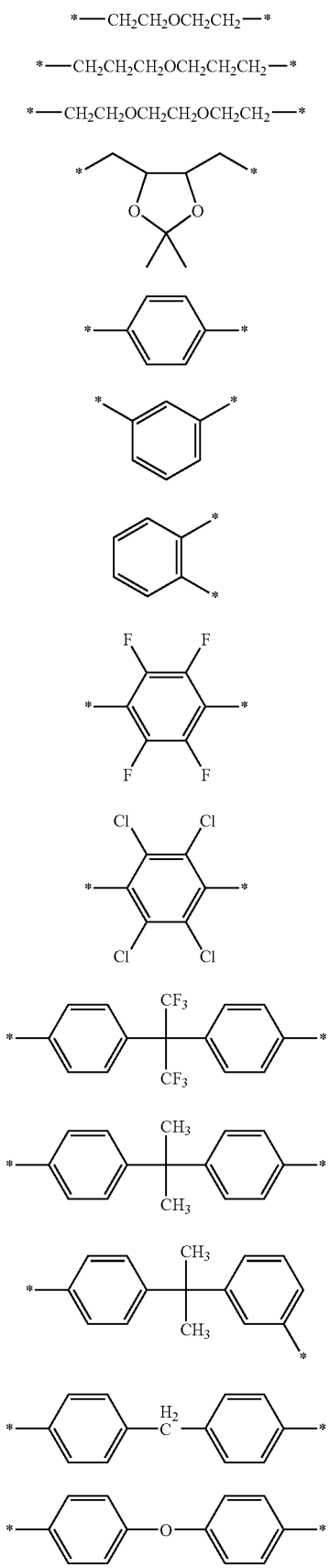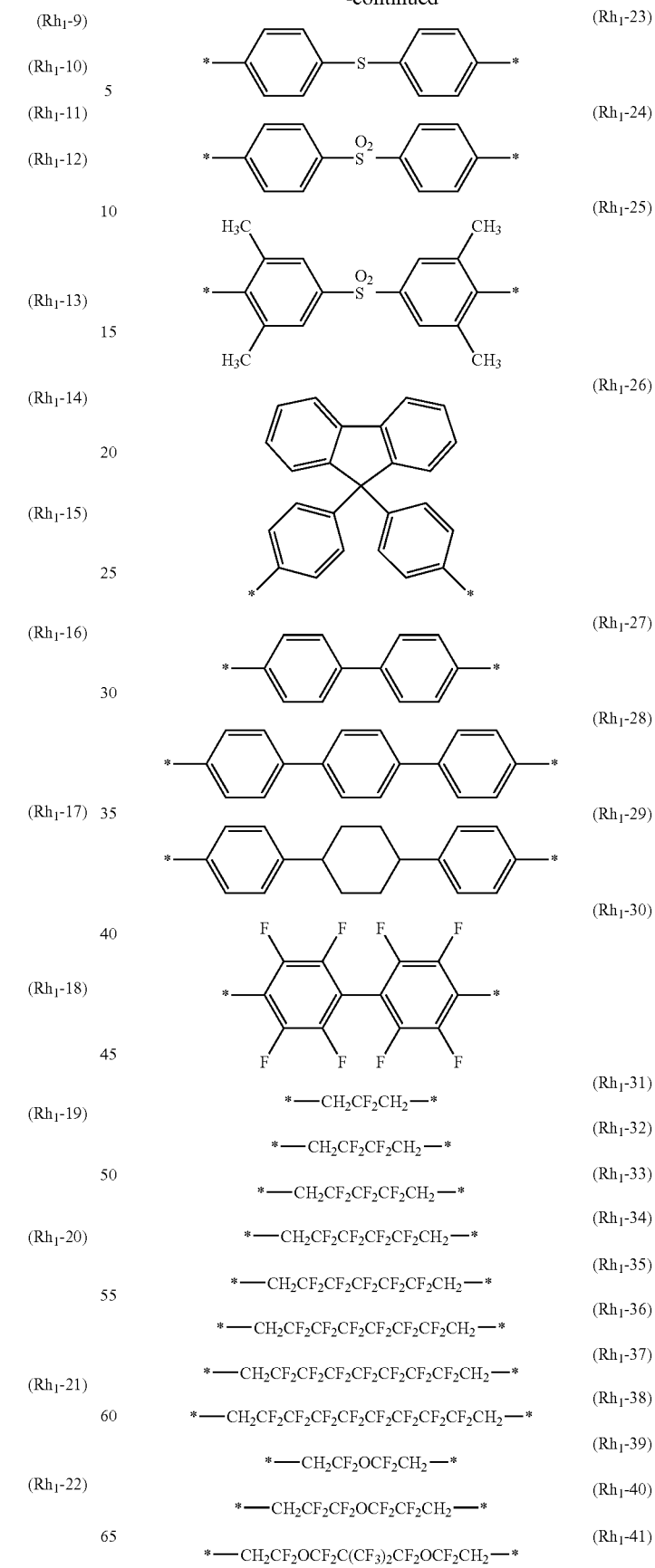

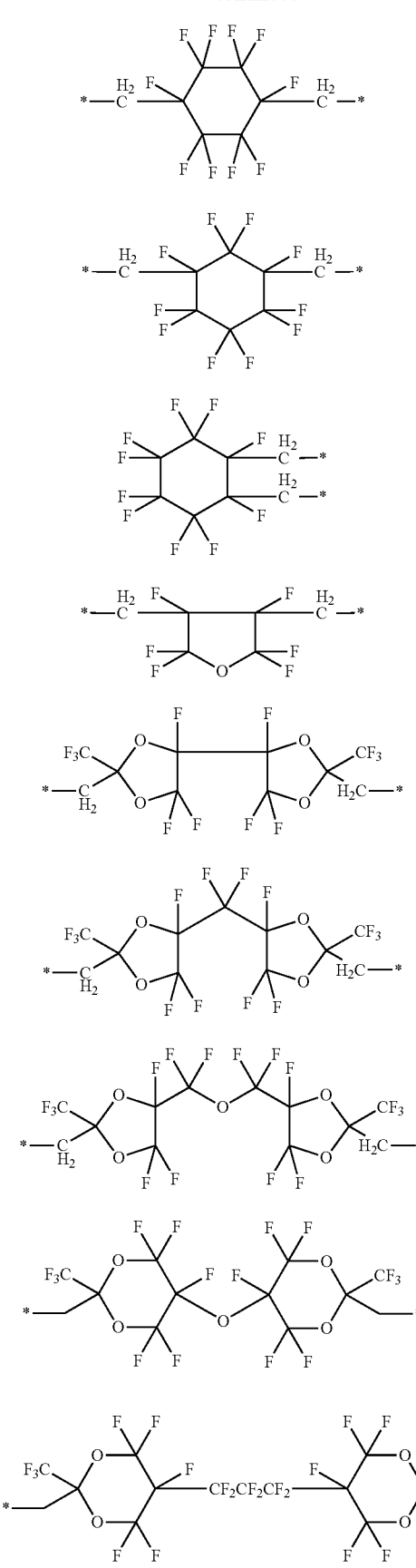

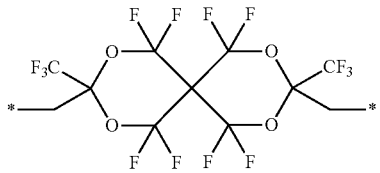

In Formula (I), $Rf_2$ represents a perfluoroalkylene group, each of $Rf_3$ and $Rf_4$ independently represents a fluorine atom, a perfluoroalkyl group or a perfluoroalkoxy group, and any two of $Rf_2$, $Rf_3$ and $Rf_4$ may be combined with each other to form a ring.

The perfluoroalkylene group represented by $Rf_2$ is preferably a perfluoroalkylene group having 1 to 30 carbon atoms, which may be linear, branched or cyclic, and which may have an ether bond in the chain. The perfluoroalkylene group has more preferably 1 to 20 carbon atoms, and still more preferably 2 to 10 carbon atoms.

The perfluoroalkyl group represented by $Rf_3$ and $Rf_4$ is preferably a perfluoroalkyl group having 1 to 30 carbon atoms, which may be linear, branched or cyclic, and which may have an ether bond in the chain. The perfluoroalkyl group has more preferably 1 to 20 carbon atoms, and still more preferably 2 to 10 carbon atoms.

The perfluoroalkoxy group represented by $Rf_3$ and $Rf_4$ is preferably a perfluoroalkoxy group having 1 to 30 carbon atoms, which may be linear, branched or cyclic, and which may have an ether bond in the chain. The perfluoroalkoxy group has more preferably 1 to 20 carbon atoms, and still more preferably 2 to 10 carbon atoms.

In Formula (I), it is preferred that both of $Rf_3$ and $Rf_4$ be fluorine atoms or perfluoroalkoxy groups. When $Rf_2$ and $Rf_3$ are both perfluoroalkoxy groups, the compound represented by formula (I) is more preferably a compound represented by the following Formula (II).

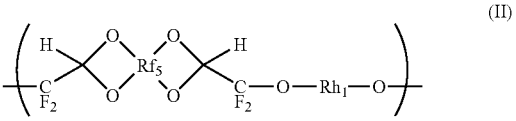

In Formula (II), $Rf_5$ represents a tetravalent perfluorinated linkage group. The tetravalent perfluorinated linkage group represented by $Rf_5$ is preferably a perfluoroalkylene group having 1 to 30 carbon atoms, which may be linear, branched or cyclic, and which may have an ether bond in the chain. The perfluoroalkylene group has more preferably 4 to 20 carbon atoms, and still more preferably 5 to 10 carbon atoms.

In the present invention, the fluorine-containing ether compounds each having a repeating unit represented by Formula (I) or (II), which have not yet been fluorinated, are novel compounds that have not yet been described in any document.

Specific examples of the compounds each having a repeating unit represented by Formula (I) or (II) will be shown below, but the present invention is not limited thereto. In the following formulae, the moiety of $Rh_1$ may be, for example, any combination of the above-mentioned examples.

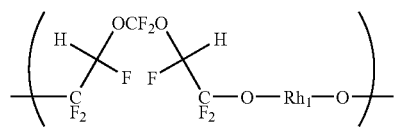 (I-1)
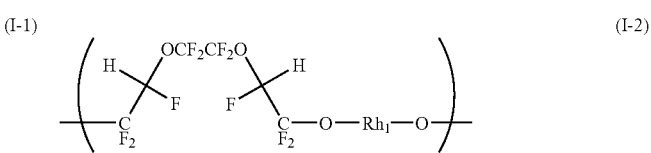 (I-2)
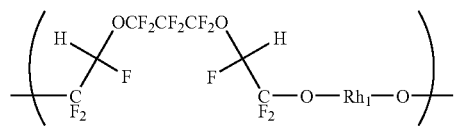 (I-3)
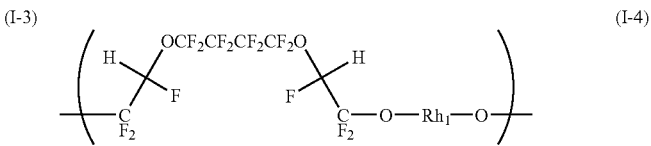 (I-4)
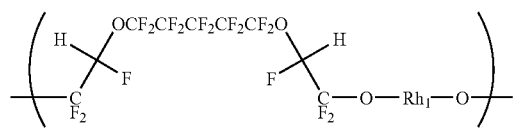 (I-5)
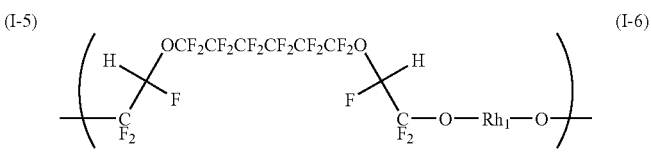 (I-6)
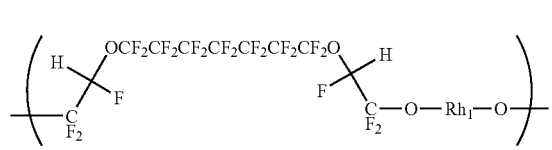 (I-7)
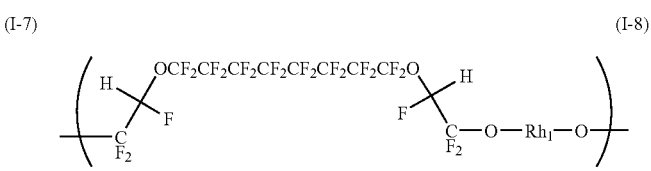 (I-8)
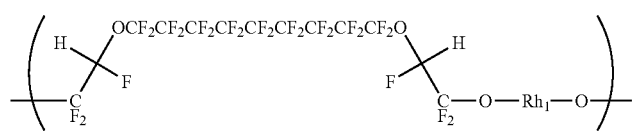 (I-9)
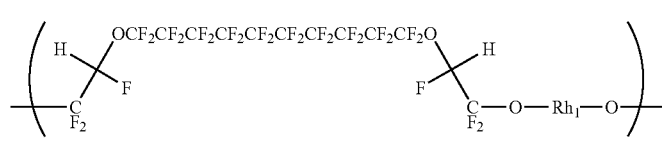 (I-10)
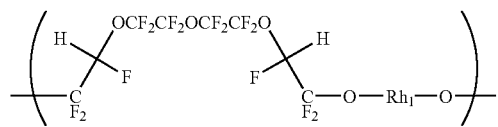 (I-11)
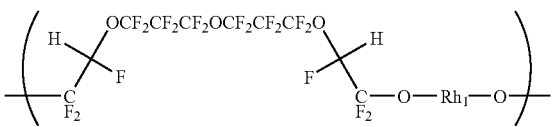 (I-12)
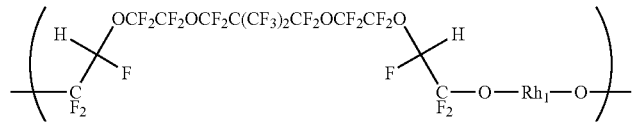 (I-13)
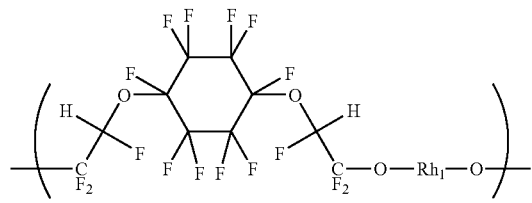 (I-14)
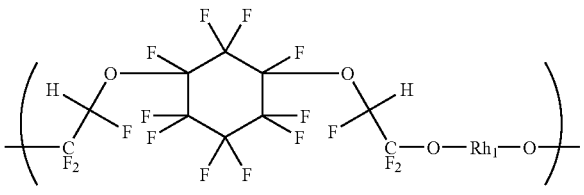 (I-15)

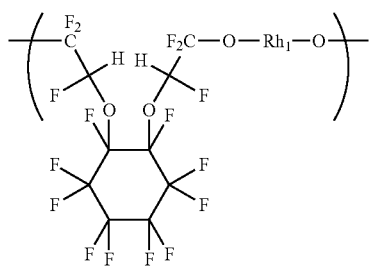 (I-16)

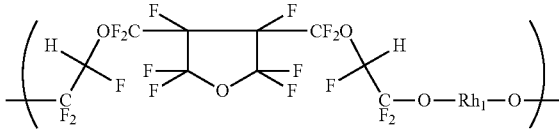 (I-17)

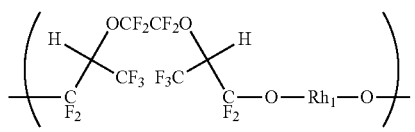 (I-18)

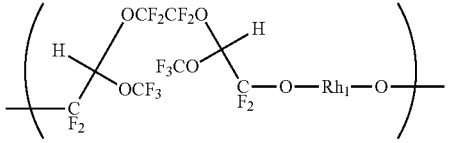 (I-19)

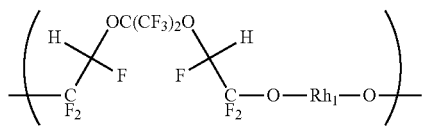 (I-20)

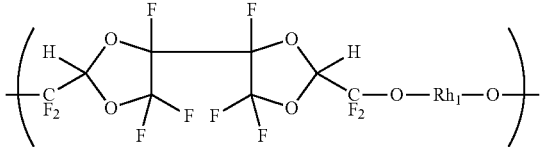 (II-1)

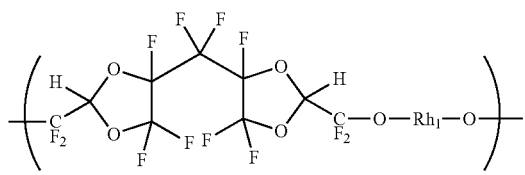 (II-2)

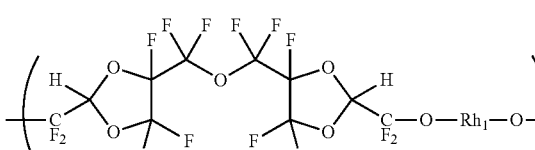 (II-3)

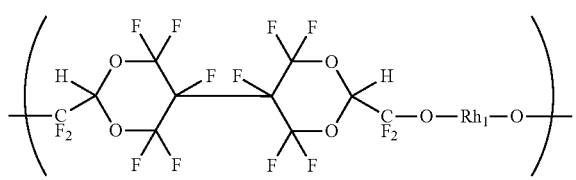 (II-4)

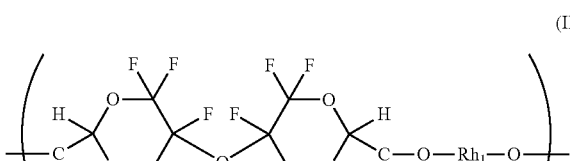 (II-5)

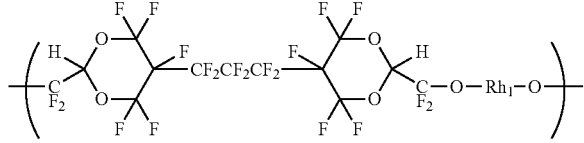 (II-6)

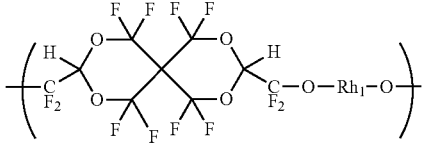 (III)

The fluorine-containing ether compounds according to the present invention are available by fluorination of compounds each having a repeating unit represented by Formula (I) (preferably a repeating unit represented by Formula (II), and more preferably a repeating unit represented by Formula (III) described in the above specific examples). As used herein the term "polymer(s)" also includes polymers having low polymerization degrees, i.e., oligomers. The molecular weights of the polymers are not particularly limited, but, in terms of number-average molecular weight, are preferably 1,000 to 500,000, and more preferably 10,000 to 100,000.

The present invention can be applied not only to the polymers but also to monomer molecules. Specifically, a compound represented by Formula (V) is fluorinated to give a perfluorinated compound represented by Formula (IV).

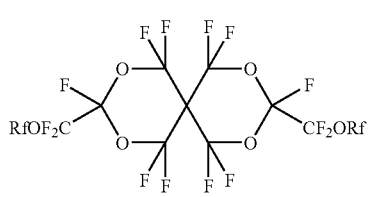 (IV)

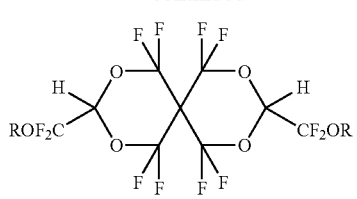

(V)

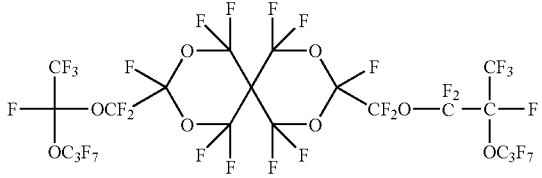

(IV-6)

wherein Rf represents a perfluoroalkyl group having 1 to 30 carbon atoms, which may be linear, branched or cyclic, and which may have an ether bond in its chain. The perfluoroalkyl group has preferably 1 to 20 carbon atoms, and still more preferably 2 to 10 carbon atoms. R represents a fluorine-containing alkyl group that is converted into Rf by fluorination. R is preferably a group represented by —CH(Rf')Rf'' (where Rf' represents a hydrogen atom or a perfluoroalkyl group, and Rf'' represents a perfluoroalkyl group) or —Ar (where Ar represents an aryl group), and is more preferably a group represented by —CH₂Rf''.

Specific examples of the compounds represented by Formula (IV) will be shown below, but the present invention is not limited thereto.

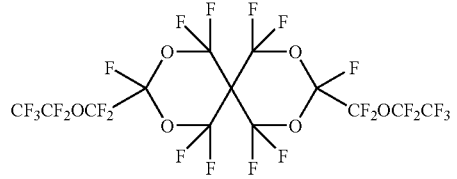

(IV-1)

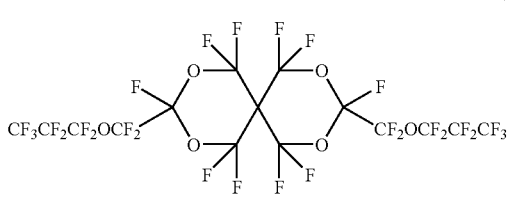

(IV-2)

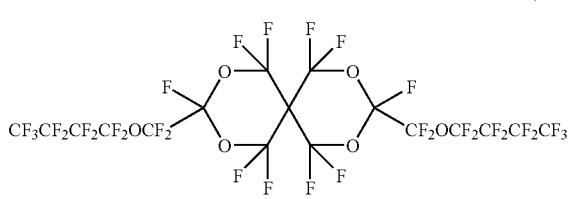

(IV-3)

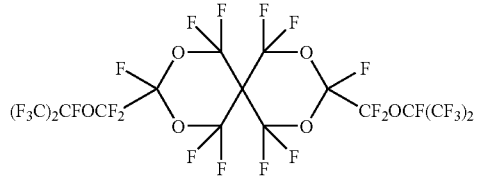

(IV-4)

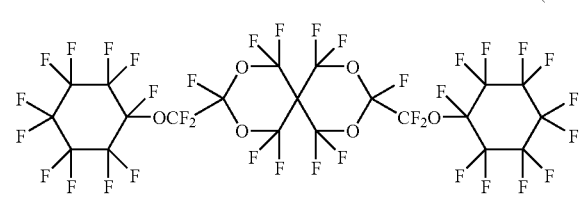

(IV-5)

Various methods for fluorination are known and examples thereof include a method of using cobalt trifluoride, a method of carrying out a fluorination reaction using, as a fluorine source, hydrogen fluoride generated by electrolysis in an electrolytic bath (hereinafter, referred to as electrolytic fluorination), and a method of carrying out fluorination directly in a liquid phase using a fluorine gas (hereinafter, referred to as liquid-phase direct fluorination). Any one of these methods may be used for substituting hydrogen atom in the fluorine-containing compound by fluorine atom. However, the method of using cobalt trifluoride and the method of using fluorination reaction by electrolytic fluorination may be more likely to cause side reactions such as cleavage of principal chain, recombination reaction, and isomerization, as compared to the liquid-phase direct fluorination reaction. Accordingly, use of liquid-phase direct fluorination reaction is more preferable for the fluorination in the present invention.

In the present invention, the liquid-phase direct fluorination reaction is preferably performed in a similar manner to the method described in U.S. Pat. No. 5,093,432, i.e., by a method of supplying a compound represented by formula (I) (preferably a compound represented by Formula (II), and more preferably a compound represented by Formula (III) described in the above specific examples) and fluorine gas diluted with an inert gas such as nitrogen or helium (hereinafter referred to as diluted fluorine gas) simultaneously, into a solvent saturated with fluorine. The raw material fluorine-containing polymer may be added, after it has been diluted in a solvent, or as it is without dilution when the polymer is in the form a liquid. The polymer is preferably dissolved in a suitable solvent before being supplied to the reaction system.

Any diluent solvent can be used herein as long as the diluent solvent dissolves the raw material fluorine-containing polymer therein. However, the following points need to be taken into consideration: when the solvent contain a hydrogen atom or an unsaturated bond, the fluorine gas is consumed also in the reaction with the solvent containing hydrogen atom and/or an unsaturated bond; and when the solvent has a relatively low boiling point, there is a concern that a solvent may vigorously react (burn) with the fluorine gas in a gas phase. Examples of preferable diluent solvent include: fluorine-containing hydrocarbon-based solvent (for example, 1H-perfluorohexane, 1H,6H-perfluorohexane, 1H,1H,2H-perfluorohexene-1-ene); fluorine-containing ether-based solvent (for example, methylnanofluorobutyl ether, 1,1,2,2-tetrafluoroethyl-2,2,3,3-tetrafluoropropyl ether, 1,1,2,3,3,3-hexafluoropropylmethyl ether, and 2-(1,1,2,3,3,3-hexafluoropropyl)tetrahydrofuran); fluorine-containing ketone-based solvent (for example, 3,3,4,4,5,5,5-heptafluoropentane-2-one, 4,4,5,5,6,6,6-heptafluorohexane-2-one, heptafluorobutylphenone, and methylperfluorobutyl ketone); fluorine-containing ester-based solvent (for example, ethylpentafluoropropionate, ethylhexafluorobutyrate, methylheptafluoroisobutyrate, dimethyloctafluoroadipate, methylperfluoroheptanoate, methyl-7H-methylperfluoroheptanoate, dimethyloctafluorosuccinate, trifluoroethyltrifluoroethyl acetate, and methyl-2,3,3,3-tetrafluoro-2-(heptafluoropropoxy)propionate); fluorine-containing benzene-based solvent (for example, hexafluorobenzene, benzotrifluoride, 1,3-bis(trifluoromethyl)benzene, 1,4-bis(perfluoroisopropyl)benzene, 1,3-bis(1,1,2,2-tetrafluoroethoxy)benzene, 1,4-bis(2,2,2-trifluoroethoxy)benzene, and decafluorobiphenyl); and mixture solvents thereof.

In addition to the diluent solvent, another solvent is used in the liquid-phase direct fluorination reaction for saturating the reaction system with the fluorine gas beforehand (hereinafter simply referred to as fluorinated solvent). The fluorinated solvent should be a solvent that does not react with the fluorine gas under the reaction condition, i.e., a solvent containing no carbon-hydrogen (C—H) bond and no carbon-carbon unsaturated bond; and preferable examples thereof include perfluoroalkanes, and perfluorinated compounds having one or more atoms selected from a chlorine atom, a nitrogen atom, and an oxygen atom in the structure.

Examples of the solvent include a perfluoroalkane compound (FC-72 (trade name, manufactured by Sumitomo 3M Limited) or the like), a perfluoroether compound (FC-75, FC-77 (both of which are trade names, manufactured by Sumitomo 3M Limited) or the like), a perfluoropolyether compound (trade name: Krytox® (registered trademark of Du Pont Kabushiki Kaisha), Fomblin® (registered trademark of AUSIMONT), Galden® (registered trademark of AUSIMONT), DEMNUM (DAIKIN INDUSTRIES, Ltd.), or the like), chlorofluorocarbons (CFC-11, CFC-113, or the like), a chlorofluoropolyether compound, a perfluorotrialkylamine compound, and an inactivated fluid (trade name: Fluorinert® (registered trademark of Sumitomo 3M Limited)).

The amount of the fluorinated solvent is preferably 50 to 1,000 times, and more preferably 100 to 500 times the weight of the raw material fluorine-containing polymer to be added.

In the reaction, the reaction temperature is preferably −78° C. to 100° C., more preferably −50° C. to 80° C., and still more preferably −20° C. to 50° C. The reaction pressure is preferably atmospheric pressure to 2 MPa, and more preferably atmospheric pressure.

When the raw material fluorine-containing polymer and the diluted fluorine gas (hereinafter also simply referred to as fluorine gas) are fed simultaneously into a solvent saturated with fluorine, the amount in molar ratio of the fluorine gas is preferably 0.5 to 10 times, more preferably 1 to 3 times, and still more preferably 1 to 2 times with respect to a theoretical amount necessary for perfluorination of the raw material fluorine-containing polymer and the diluent solvent.

When the fluorination does not sufficiently proceed after supplying the raw material fluorine-containing polymer, the fluorination of the raw material fluorine-containing polymer can be promoted by supplying a compound such as the above-mentioned fluorine-containing diluent solvent together with the fluorine gas, or by irradiating the reaction system with an ultraviolet ray while supplying the fluorine gas.

Hydrogen fluoride is generated as a byproduct along with the progress of the fluorination reaction. In order to remove the hydrogen fluoride, it is preferable to add a hydrogen fluoride scavenger to the reaction system or bring the discharge gas into contact with a hydrogen fluoride scavenger at the reactor gas outlet. Examples of the hydrogen fluoride scavengers include organic bases such as trialkylamines, and alkali metal fluorides such as NaF and KF. The hydrogen fluoride scavenger is more preferably NaF.

When a hydrogen fluoride scavenger is to be coexisted in the reaction system, the amount of the hydrogen fluoride scavenger to be added is preferably 1 to 10 times, and more preferably 2 to 5 times the theoretical amount of fluorine atoms to be generated.

The method of synthesizing the raw material fluorine-containing polymer represented by Formula (I), (II) or (III) is not particularly limited. For example, the raw material fluorine-containing polymer can be obtained by conducting addition polymerization of a perfluorodiene represented by Formula (i), (ii) or (iii) with a diol represented by Formula (iv) under basic conditions. The compound represented by Formula (V) is obtained by conducting addition reaction of a compound represented by Formula (iii) with a compound represented by ROH under basic conditions. The details of the methods of synthesizing the compound having a repeating unit represented by Formula (I) or (II) or the compound represented by Formula (III) are described in JP-A-2007-007514, which are schematically illustrated below.

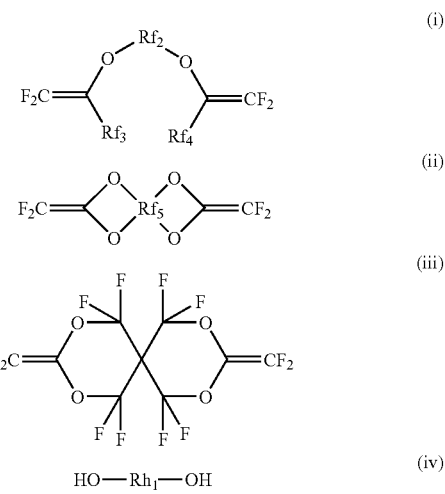

The compounds each represented by Formulae (i), (ii) and (iii) can be synthesized, for example, by using liquid-phase fluorination reaction as a key reaction. For example, the synthesis route of the compound represented by Formula (i) is illustrated below by way of examples.

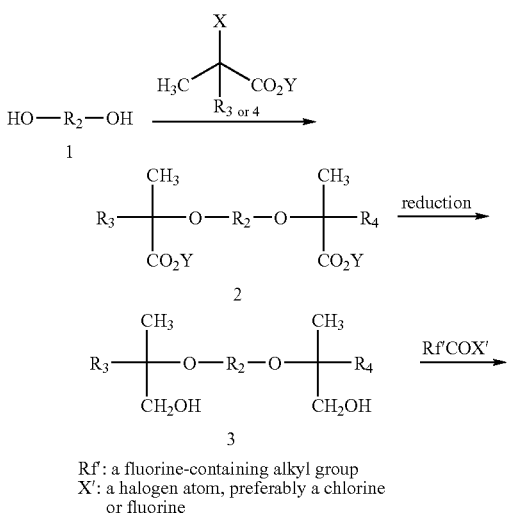

Rf': a fluorine-containing alkyl group
X': a halogen atom, preferably a chlorine or fluorine -continued

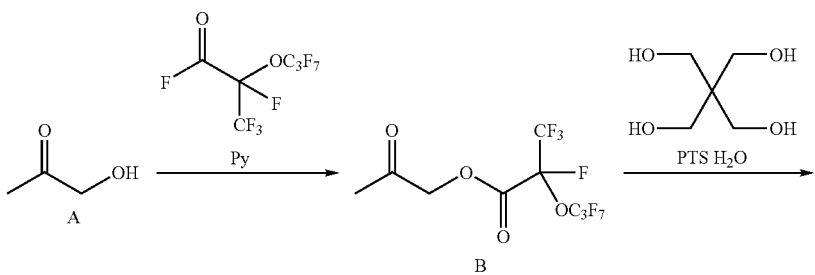

Z: F, OM (M represents an alkaline metal), and the like

Ri: a group which can be converted into a Rfi group by fluorination reaction (i represents an integer of 2 to 4)
X: a halogen atom, preferably a chlorine or a bromine
Y: a hydrogen atom, an alkaline metal, an alkyl group, and the like Details of the respective steps may be set with reference to, for example, JP-T-4-500520 ("JP-T" means a published Japanese translation of PCT international application), International Patents Nos. WO 00/56694 A and WO 02/004397, JP-T-2003-518051, and documents cited in these documents.

Among highly fluorinated compounds, the compounds according to the present invention have particularly high fluorine contents, and whose structures are variable according to desired physical properties. Those fluorine-containing ether compounds with high fluorine contents can be obtained efficiently. Those highly fluorinated polymers are expected to have properties specific to fluorine-containing compounds, such as low refractive index, low dielectric constant, water- and oil-repellency, low hygroscopicity, chemical resistance, non-adhesiveness, low frictional properties, and electrical insulation properties, and are also applicable as transparent materials.

The present invention will be described in more detail based on the following examples, but the present invention is not limited thereto.

EXAMPLES

Synthesis of Materials

Perfluorodiene (iii) and fluorine-containing diol (iv-1) were synthesized according to the following schemes:

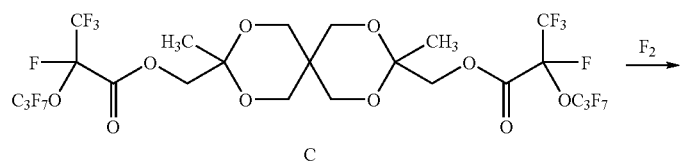

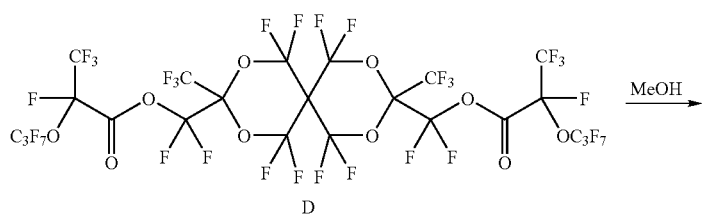

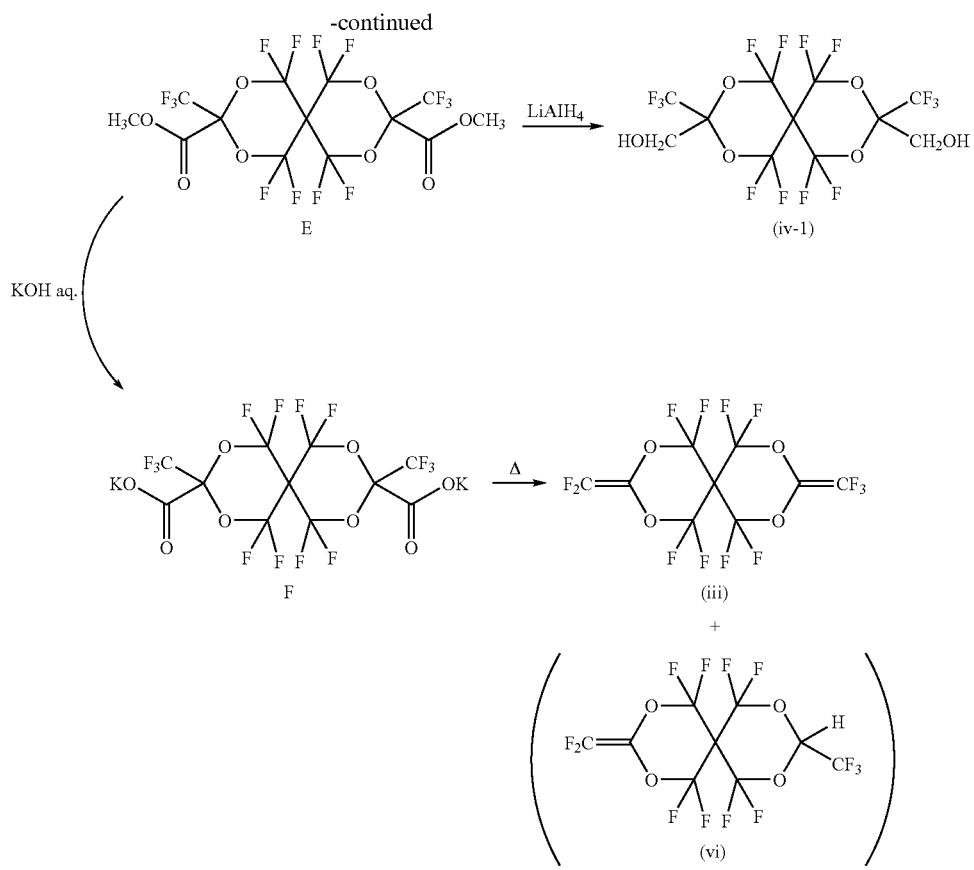

Synthesis of Compound B

To a solution of hydroxyacetone (7.4 g) and pyridine (8.1 ml) in ethyl acetate (100 ml), undecafluoro-(2-methyl-3-oxa-hexanoic acid)fluoride (10 g) was added dropwise at room temperature (25° C.). After stirring at room temperature for 2 hours, the reaction mixture was poured into diluted hydrochloric acid. After separation, the organic layer was washed with water and a saturated sodium chloride solution and dried with magnesium sulfate. The concentrated residue was purified by column chromatography (developing solvent: ethyl acetate/hexane), to obtain Compound B (10.2 g, 88%).

$^1$H NMR (CDCl$_3$) δ 2.22 (s, 3H), 4.85 (d, J=16.2 Hz, 1H), 4.96 (d, J=16.2 Hz, 1H)

$^{19}$F NMR (CDCl$_3$) δ −80.3 (1F), −81.8 (3F), −82.5 (3F), −86.7 (1F), −130.2 (2F), −132.8 (1F)

Synthesis of Compound C

Compound B (9.9 g), pentaerythritol (1.74 g), p-toluenesulfonic acid monohydrate (0.25 g) and toluene (50 ml) were refluxed for 4 hours while conducting dehydration. The reaction mixture was washed with an aqueous sodium hydrogen carbonate solution, water and a saturated sodium chloride solution, and then dried with sodium sulfate. The concentrated residue was purified by column chromatography (developing solvent: ethyl acetate/hexane), to obtain Compound C (5.9 g, 53%).

$^1$H NMR (CDCl$_3$) δ 1.41 (s, 3H), 3.64 to 3.85 (m, 4H), 4.31 (d, J=11.1 Hz, 1H), 4.48 (d, J=11.1 Hz, 1H)

$^{19}$F NMR (CDCl$_3$) δ−80.2 (1F), −81.7 (3F), −82.5 (3F), −86.8 (1F), −130.1 (2F), −132.3 (1F)

Synthesis of Compound D

FC-72 (180 ml) and sodium fluoride (10 g) were placed in a 300-ml Teflon® container equipped with a raw material inlet, a fluorine inlet, a helium gas inlet and an air outlet that was connected via a reflux apparatus cooled with dry ice to a fluorine trap. Helium gas was introduced, at a flow rate of 50 ml/min, into the container at an inner temperature of 20° C. for 30 minutes while stirring. Sequentially, a 20% F$_2$/N$_2$ gas was introduced thereinto at a flow rate of 100 ml/min for 30 minutes. Then, while maintaining the fluorine flow rate as above, a solution of Compound C (4.25 g) in FC-72 (13.5 ml) was added at a rate of 6.2 ml/hr, and a solution of hexafluorobenzene (1 g) in FC-72 (5 ml) was added at the same rate. Next, a 20% F$_2$/N$_2$ gas was introduced thereinto at a flow rate of 100 ml/min for 30 minutes, and helium gas was additionally introduced at a rate of 200 ml/min for 30 minutes, and insoluble matter was removed by filtration. The reaction mixture was concentrated under atmospheric pressure, and further concentrated under reduced pressure, to obtain Compound D (5.1 g, crude yield: 88%) as a substantially single product.

$^{19}$F NMR (CDCl$_3$) δ −60.6 to −64.4 (m, 8F), −76.7 (s, 6F), −79.8 to −80.0 (m, 1F), −80.3 to −80.6 (m, 1F), −82.0 (m, 6F), −82.1 (s, 6F), −83.4 to −83.8 (m, 4F), −86.7 (bs, 1F), −86.9 (bs, 1F), −130.2 (s, 4F), −132.0 (s, 1F), −132.1 (s, 1F)

Synthesis of Compound E

The crude Compound D (5.1 g) obtained above was added dropwise to a dispersion of sodium fluoride (10 g) in methanol (200 ml), followed by stirring at room temperature for 3 hours. After removing insoluble matter by filtration, the filtrate was concentrated to about 30 ml and extracted with a solution of sodium hydrogen carbonate and ethyl acetate. The organic layer was washed with water and a saturated sodium chloride solution and dried with magnesium sulfate. The concentrated residue was purified by column chromatography (developing solvent: ethyl acetate/hexane), to obtain Compound E (1.8 g, 78%).

$^1$H NMR (CDCl$_3$) δ 3.99 (s, 3H)
$^{19}$F NMR (CDCl$_3$) δ −62.5 to −63.8 (m, 4F), −69.9 to −71.3 (m, 4F), −81.2 (s, 3F), −81.4 (s, 3F)

Synthesis of Fluorine-Containing Diol (iv-1)

To a solution of Compound E (0.28 g) in diethyl ether (10 ml), lithium aluminum hydride (0.038 g) was added at 5° C. After stirring at room temperature for 4 hours, the reaction mixture was gradually added with diluted hydrochloric acid. After the mixture was extracted with ethyl acetate, the organic layer was washed with water and a saturated sodium chloride solution, and dried with magnesium sulfate. The concentrated residue was purified by column chromatography (developing solvent: ethyl acetate/hexane), to obtain Compound (iv-1) (0.2 g, 80%).

$^1$H NMR (CDCl$_3$) δ 2.20 (bs, 1H), 4.21 (bs, 2H)
$^{19}$F NMR (CDCl$_3$) δ −56.2 to −58.6 (m, 4F), −66.0 to −67.3 (m, 4F), −80.9 to −81.0 (m, 6F)

Synthesis of Perfluorodiene (iii)

To a solution of Compound E (16.2 g) in methanol (200 ml) and water (40 ml), 10 ml of an 8 N aqueous potassium hydroxide solution was added dropwise, at room temperature. The reaction mixture was stirred at room temperature for 2 hours, and the solvent was distilled off under reduced pressure. The concentrated residue was added with 30 ml of water, and further added dropwise with concentrated hydrochloric acid until the mixture became acidic on a pH indicator paper. The precipitated white crystals were filtered, dispersed in water (30 ml), and added dropwise with a 1 N aqueous potassium hydroxide solution to thereby adjust a pH to 8. The reaction mixture was concentrated under reduced pressure, the residue was thoroughly dried at 100° C. using a vacuum pump, to obtain Compound F (16.5 g, 93%). The obtained Compound F was thermally decomposed at 280° C. under reduced pressure (4 mmHg), and volatile components were collected by a trap at −78° C. This procedure was repeated, the collected liquids were combined, distilled under reduced pressure, and thereby yielded crude material (20 g) of Compound (iii). The crude material had a purity by gas chromatography of 95%, with the residual 5% being a monoene (vi). To a solution of the crude material (15 g) of Perfluorodiene (iii) in anhydrous diethyl ether (150 ml), a 1.6 M solution of lithium bis(trimethylsilyl)amide in THF (3 ml) was added dropwise at 5° C. in a nitrogen atmosphere. After stirring at room temperature for 16 hours, diluted hydrochloric acid was poured to stop the reaction. The organic layer was washed with an aqueous sodium chloride solution three times, and the solvent was distilled off at 40° C. to 80° C. Purification by distillation at further elevated temperatures under atmospheric pressure produced Perfluorodiene (iii) (9.6 g) with a purity by gas chromatography of 99% or more.

$^{19}$F NMR (CDCl$_3$) δ −70.7 (s, 8F), −111.2 (s, 4F), b.p. 55° C. (20 mmHg)

Synthesis of Fluorine-Containing Polymer (iii-1) by Polymerization of Perfluorodiene (iii) and Fluorine-Containing Diol (iv-1)

A solution of the crude material (1.12 g) of Perfluorodiene (iii), Fluorine-containing Diol (iv-1) (1.34 g), tetrabutylammonium bromide (0.18 g), acetonitrile (1 ml), benzotrifluoride (10 ml) and potassium hydroxide (0.32 g) in water (10 ml) was mixed and stirred at 50° C. for 41 hours. After cooling to room temperature, the mixture was separated. The organic layer was washed with water, dried with magnesium sulfate, and concentrated under reduced pressure. The concentrated residue (2.1 g) was dissolved in acetone (2 ml), reprecipitated with methanol (300 ml), and dried, to obtain 0.5 g of white crystals. The obtained crystals were dissolved in deuterated chloroform and subjected to analyses by $^1$H-NMR and $^{19}$F-NMR, to find that the crystals were a polymer (iii-1) having the following repeating unit and contains no unsaturated bond formed by removal of hydrogen fluoride.

Mw: 11,000 in terms of polystyrene
$^1$H NMR (CDCl$_3$) δ 4.90 (bs, 4H), 6.44 (bs, 2H)
$^{19}$F NMR (CDCl$_3$) δ −57.5 to −73.5 (m, 16F), −81.7 (s, 6F), −88.7 to −89.3 (s, 4F)

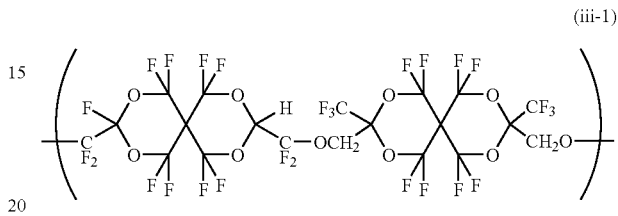

(iii-1)

Synthesis of Fluorine-Containing Polymer (iii-2) by Polymerization of Perfluorodiene (iii) and 2,2,3,3-Tetrafluorobutanediol (iv-2)

Perfluorodiene (iii) (8.08 g), 2,2,3,3-Tetrafluorobutanediol (iv-2) (3.31 g), potassium carbonate (6.05 g), and acetonitrile (100 ml) were mixed and stirred at room temperature for 64 hours. The reaction mixture was poured into ethyl acetate (300 ml) and water (300 ml), and separated. The organic layer was washed with a sodium chloride solution three times and dried with magnesium sulfate. The solvent was distilled off under reduced pressure to obtain an amorphous polymer (11.4 g). The polymer was dissolved in acetone (40 ml), reprecipitated with chloroform (2,000 ml), and dried, to obtain 7.85 g of an amorphous polymer. The obtained polymer was dissolved in deuterated chloroform and subjected to analyses by $^1$H-NMR and $^{19}$F-NMR, to find that the polymer was a polymer (iii-2) having the following repeating unit and contained no unsaturated bond formed by removal of hydrogen fluoride.

Mw: 33,000 in terms of polystyrene, Mw/Mn: 2.2
$^1$H NMR (CDCl$_3$) δ 4.73 (t, J=13.8 Hz, 4H), 6.41 (s, 2H)
$^{19}$F NMR (CDCl$_3$) δ −67.8 to −73.4 (m, 8F), −87.7 to −89.3 (m, 4F), −122.7 (t, J=13.8 Hz, 4F)

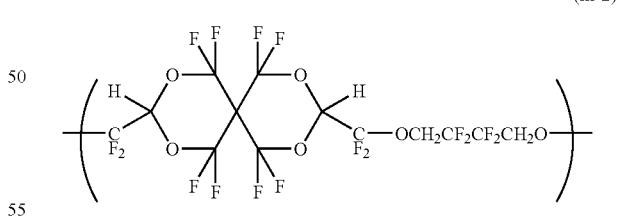

(iii-2)

Synthesis of Fluorine-Containing Compound (V-1) by Reaction of Perfluorodiene (iii) with Trifluoroethanol The crude material (4.0 g) of Perfluorodiene (iii), trifluoroethanol (2.1 g), potassium carbonate (3.1 g) and acetonitrile were mixed and stirred at room temperature for 4 hours. The reaction mixture was poured into ethyl acetate (150 ml) and water (150 ml), and separated. The organic layer was washed with a sodium chloride solution twice, dried with magnesium sulfate, from which the solvent was distilled off under reduced pressure. By removing a by-product derived from the Monoene (vi) by column chromatography (developing solvent: ethyl acetate/hexane=1/9), a fluorine-containing compound (5.3 g) represented by the following Formula (V-1) was obtained.

$^1$H NMR (CDCl$_3$) δ 4.32 (q, J=7.8 Hz, 4H), 5.60 (s, 2H)
$^{19}$F NMR (CDCl$_3$) δ −68.1 to −73.0 (m, 8F), −74.4 (t, J=7.8 Hz, 6F), −88.1 (s, 4F)

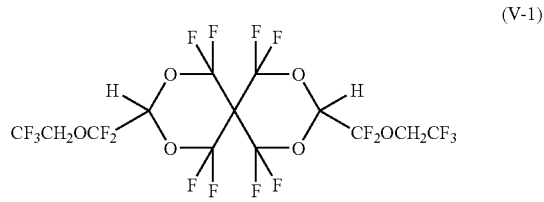

Example 1

Synthesis of Perfluorinated Compound (IV-1) by Fluorination of Fluorine-Containing Compound (V-1)

FC-72 (180 ml) and sodium fluoride (2.5 g) were placed in a 300-ml Teflon® container equipped with a raw material inlet, a fluorine inlet, a helium gas inlet and an air outlet that was connected via a reflux apparatus cooled with dry ice to a fluorine trap. Helium gas was introduced, at a flow rate of 50 ml/min, into the container at an inner temperature of 0° C. for 30 minutes while stirring. Sequentially, a 20% F$_2$/N$_2$ gas was introduced thereinto at a flow rate of 100 ml/min for 30 minutes. Then, while maintaining the fluorine flow rate as above, a solution of Fluorine-containing Compound (V-1) (3.0 g) in FC-72 (5 ml) was added at a rate of 10 ml/hr, and a solution of hexafluorobenzene (2.1 g) in FC-72 (8 ml) was added at a flow rate of 4.5 ml/hr. Next, a 20% F$_2$/N$_2$ gas was introduced thereinto at a flow rate of 100 ml/min for 30 minutes, and helium gas was additionally introduced at a rate of 200 ml/min for 1 hour, and insoluble matter was removed by filtration. FC-72 was distilled off under atmospheric pressure. The residue was analyzed by NMR using hexafluorobenzene as an internal standard to find that a Perfluorinated Compound (IV-1) was quantitatively produced. Further, the residue was purified by distillation under reduced pressure to obtain 2.6 g of Perfluorinated Compound (IV-1). Perfluorinated Compound (IV-1) had a refractive index of 1.30 as determined with an Abbe refractometer, which was lower than that (1.36) of the Raw Material Compound (V-1).

$^{19}$F NMR (CDCl$_3$) δ −57.8 to −73.0 (m, 8F), −86.5 (s, 6F), −87.2 (t, J=14.1 Hz, 2F), −88.1 (m, 4F), −88.4 (m, 4F), b.p.=55° C. (5 mmHg)

Example 2

Fluorination of Fluorine-Containing Polymer (iii-1)

FC-72 (180 ml) and sodium fluoride (9.3 g) were placed in a 300-ml Teflon® container equipped with a raw material inlet, a fluorine inlet, a helium gas inlet and an air outlet that was connected via a reflux apparatus cooled with dry ice to a fluorine trap. Helium gas was introduced, at a flow rate of 50 ml/min, into the container at an inner temperature of 0° C. for 30 minutes while stirring. Sequentially, a 20% F$_2$/N$_2$ gas was introduced thereinto at a flow rate of 100 ml/min for 30 minutes. Then, while maintaining the fluorine flow rate as above, a solution of Fluorine-containing Compound (iii-1) (0.5 g) in a mixture of solvents of hexafluorobenzene (2.5 g) and methyl tridecafluoroheptanoate (2.5 g) was added at a rate of 2.9 ml/hr, and a solution of hexafluorobenzene (1.6 g) was added. Next, a 20% F$_2$/N$_2$ gas was introduced thereinto at a flow rate of 100 ml/min for 30 minutes, and helium gas was additionally introduced at a rate of 200 ml/min for one hour, and insoluble matter was removed by filtration. By removing volatile components under reduced pressure and by drying, an amorphous polymer (0.4 g) was obtained. The amorphous polymer was analyzed by NMR in a hexafluorobenzene/chloroform system, to find that all protons derived from the raw material had disappeared, indicating that the amorphous polymer was a polymer having the following repeating unit. The obtained amorphous polymer had a 10% by mass reduction temperature at a temperature elevation rate of 10° C./min of 450° C. determined by thermal analysis, which was higher than that of the Raw Material Polymer (iii-1) (380° C.), indicating that the produced polymer had higher thermal stability.

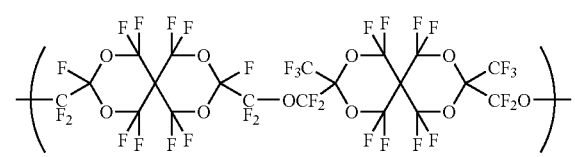

Example 3

Fluorination of Fluorine-Containing Polymer (iii-2)

FC-72 (180 ml) and sodium fluoride (9.3 g) were placed in a 300-ml Teflon® container equipped with a raw material inlet, a fluorine inlet, a helium gas inlet and an air outlet that was connected via a reflux apparatus cooled with dry ice to a fluorine trap. Helium gas was introduced, at a flow rate of 50 ml/min, into the container at an inner temperature of 0° C. for 30 minutes while stirring. Sequentially, a 20% F$_2$/N$_2$ gas was introduced thereinto at a flow rate of 100 ml/min for 30 minutes. Then, while maintaining the fluorine flow rate as above, a solution of Fluorine-containing Compound (iii-2) (1 g) in a mixture of solvents of hexafluorobenzene (2.5 g) and methyl tridecafluoroheptanoate (2.5 g) was added at a rate of 2.8 ml/hr, and a solution of hexafluorobenzene (1.6 g) was added at a flow rate of 0.9 ml/hr. Next, a 20% F$_2$/N$_2$ gas was introduced thereinto at a flow rate of 100 ml/min for 30 minutes, and helium gas was additionally introduced at a rate of 200 ml/min for one hour, and insoluble matter was removed by filtration. By removing volatile components under reduced pressure and by drying, a viscous oily matter (0.65 g) was obtained. Fluorine-containing Polymer (iii-2) which is a raw material had relatively high solubility in acetone and THF. In contrast, the obtained oily matter was insoluble in those solvents. The oily matter was analyzed by NMR in a hexafluorobenzene/chloroform system, to find that all protons derived from the raw material had disappeared, indicating that the oily matter was a polymer having the following repeating unit. The obtained polymer had a refractive index of 1.34 as determined with an Abbe refractometer, which was lower than that of the Raw Material Polymer (iii-2) (1.36).

$^{19}$F NMR (CDCl$_3$) δ −59.0 to −74.2 (m, 8F), −84.5 (m, 4F), −88.2 (m, 2F), −89.3 (m, 4F), −127.1 (m, 4F)

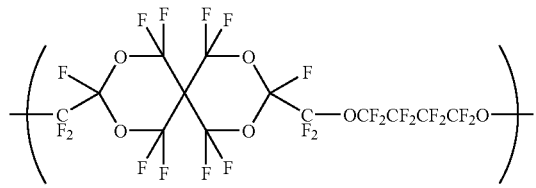

Having described our invention as related to the present embodiments, it is our intention that the invention not be limited by any of the details of the description, unless otherwise specified, but rather be construed broadly within its spirit and scope as set out in the accompanying claims.

What we claim is:

1. A fluorine-containing ether compound with a fluorine content increased, the fluorine content being enhanced by fluorinating a polymer including a repeating unit represented by the following Formula (II):

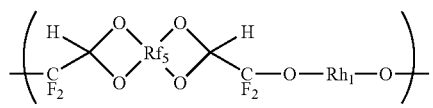

wherein Rh$_1$ represents a divalent linkage group, and Rf$_5$ represents a tetravalent perfluorinated linkage group.

2. The fluorine-containing ether compound according to claim 1, in which the repeating unit represented by Formula (II) is a repeating unit represented by the following Formula (III):

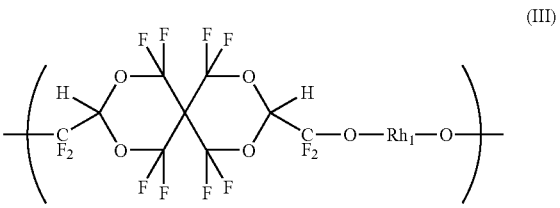

wherein Rh$_1$ is as defined above.

3. The fluorine-containing ether compound according to claim 1, wherein the fluorination is conducted by reacting a solution of a polymer having the repeating unit represented by Formula (II) and a fluorine gas.

4. The fluorine-containing ether compound according to claim 2, wherein the fluorination is conducted by reacting a solution of a polymer having the repeating unit represented by Formula (III) and a fluorine gas.

5. A perfluoroether compound represented by the following Formula (IV):

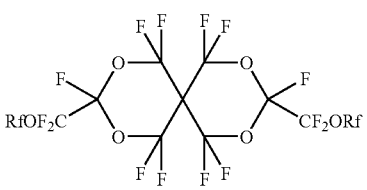

wherein R$_f$ represents a perfluoroalkyl group.

* * * * *

UNITED STATES PATENT AND TRADEMARK OFFICE
CERTIFICATE OF CORRECTION

| | | |
|---|---|---|
| PATENT NO. | : 8,106,222 B2 | |
| APPLICATION NO. | : 12/100362 | |
| DATED | : January 31, 2012 | |
| INVENTOR(S) | : Takayuki Ito and Toshimitsu Sakuma | |

It is certified that error appears in the above-identified patent and that said Letters Patent is hereby corrected as shown below:

On the Title page, left column, after Item (65), please insert the following.

Item --(30) Foreign Application Priority Data

April 12, 2007   (JP).........2007-105279--

Signed and Sealed this
Nineteenth Day of June, 2012

David J. Kappos
*Director of the United States Patent and Trademark Office*